(12) United States Patent
Darvish et al.

(10) Patent No.: US 6,292,693 B1
(45) Date of Patent: Sep. 18, 2001

(54) CONTRACTILITY ENHANCEMENT USING EXCITABLE TISSUE CONTROL AND MULTI-SITE PACING

(75) Inventors: Nissim Darvish; Itzhak Shemer, both of Haifa (IL)

(73) Assignee: Impulse Dynamics N.V., Coracao (AN)

( * ) Notice: Subject to any disclaimer, the term of this patent is extended or adjusted under 35 U.S.C. 154(b) by 0 days.

(21) Appl. No.: 09/260,769

(22) Filed: Mar. 2, 1999

Related U.S. Application Data

(60) Provisional application No. 60/104,479, filed on Oct. 16, 1998.

(51) Int. Cl.[7] .................................................. A61N 1/362
(52) U.S. Cl. .................................................. 607/9; 607/17
(58) Field of Search ..................................... 607/9, 17–24

(56) References Cited

U.S. PATENT DOCUMENTS

| | | |
|---|---|---|
| 4,543,956 | 10/1985 | Herscovici . |
| 4,554,922 | 11/1985 | Prystowsky et al. . |
| 5,205,284 | 4/1993 | Freeman . |
| 5,720,768 | 2/1998 | Verboven-Nelissen . |
| 5,800,464 | 9/1998 | Kieval ..................................... 607/9 |
| 5,871,506 | 2/1999 | Mower . |

FOREIGN PATENT DOCUMENTS

WO97/25098 * 7/1997 (WO) ....................................... 607/9

OTHER PUBLICATIONS

U.S. Patent application No. 60/104,479, Filed Oct. 16, 1998, A provisional.
PCT Patent Application No.: PCT/IL97/00233, WO/97/4437.
Israel Patent Application No: 127295, WO/97/47290.
S. Cazeau, et al., "Multisite Pacing for End–Stage Heart Failure: Early Experience", in Pacing and Clinical Electrophysiology 19 (Nov. 1996), Part II, pp. 1748–1757.
The merck Manual, Section 3, the 16th Edition of the Merck Manual, Published in 1992.
H. Antoni, et al., Polarization Effects of Sinusoidal 50–Cycle Alternating Current on Membrane Potential of Mammalian Cardiac Fibres, Pflugers Arch. 314, pp. 274–291 (1970).

* cited by examiner

Primary Examiner—Jeffrey R. Jastrzab
(74) Attorney, Agent, or Firm—Cowan, Liebowitz & Latman, P.C.; William H. Dippert

(57) ABSTRACT

A method and apparatus for stimulating cardiac tissue. Pacing pulses are applied to the heart at multiple sites in at least two different chambers of the heart; and an Excitable Tissue Control (ETC) signal is applied in a vicinity of one or more of the pacing sites following application of the pacing pulse at the site.

16 Claims, 7 Drawing Sheets

CONTRACTILITY ENHANCEMENT USING EXCITABLE TISSUE CONTROL AND MULTI-SITE PACING

RELATED APPLICATIONS

This application claims the benefit of U.S. Provisional Patent Application no. 60/104,479, filed Oct. 16, 1998, which is assigned to the assignee of the present patent application and is incorporated herein by reference.

FIELD OF THE INVENTION

The present invention relates generally to invasive devices and methods for treatment of the heart, and specifically to devices and methods for pacing and electrical stimulation of the heart muscle.

BACKGROUND OF THE INVENTION

Multi-site and bi-ventricular pacing are known in the art, primarily as methods for enhancing mechanical synchronization of the contraction of different parts of the heart muscle and reducing mitral regurgitation due to poorly-synchronized mechanical contractions. Such pacing is described, for example, in an article by S. Cazeau, et al., entitled "Multisite Pacing for End-Stage Heart Failure: Early Experience," in *Pacing and Clinical Electrophysiology* 19 (November, 1996), Part II, pages 1748–1757, which is incorporated herein by reference.

U.S. Pat. No. 5,800,464 to Kieval, which is incorporated herein by reference, describes an implantable system for effecting hyperpolarization of myocardial cells of a heart chamber, in order to enhance the relaxation thereof in the diastolic phase.

PCT patent application PCT/IL97/00012, published as WO 97/25098, to Ben-Haim et al., which is incorporated herein by reference, describes methods for modifying the force of contraction of at least a portion of a heart chamber by applying a non-excitatory electric field to the heart at a delay after electrical activation of the portion. The non-excitatory field is such as does not induce new activation potentials in cardiac muscle cells, but rather modifies the cells' response to the activation. In the context of the present patent application, the use of such a non-excitatory field is referred to as Excitable Tissue Control (ETC). The non-excitatory field may be applied in combination with a pacemaker or defibrillator, which applies an excitatory signal (i.e., pacing or defibrillation pulses) to the heart muscle.

PCT patent application PCT/IL97/00236, which is also incorporated herein by reference, describes a pacemaker that gives cardiac output enhancement. This pacemaker applies both excitatory (pacing) and non-excitatory (ETC) electrical stimulation pulses to the heart. By applying non-excitatory pulses of suitable strength, appropriately timed with respect to the heart's electrical activation, the contraction of selected segments of the heart muscle can be increased or decreased, thus increasing or decreasing the stroke volume of the heart. The PCT application suggests that pacing electrodes may be placed in two, three or all four chambers of the heart, in accordance with methods of multi-chamber pacing known in the art.

SUMMARY OF THE INVENTION

It is an object of some aspects of the present invention to provide improved methods and apparatus for applying Excitable Tissue Control (ETC) in order to enhance hemodynamic performance of the heart.

It is a further object of some aspects of the present invention to provide methods and apparatus for multi-site pacing of the heart together with ETC, so as to enhance hemodynamic performance of the paced heart.

It is yet a further object of some aspects of the present invention to provide methods and apparatus for applying ETC together with pacing of the heart, preferably multi-site pacing, so as to reduce or eliminate the possibility of generating undesirable, new propagating action potentials, which can induce arrhythmias.

In preferred embodiments of the present invention, an electrical cardiac stimulator comprises a plurality of electrodes, which are placed at multiple sites in at least two different chambers of the heart, and an electrical control unit. The control unit administers a sequence of pacing pulses to two or more of the electrodes at respective pacing sites in the different chambers. The control unit then applies an ETC signal to one or more of the electrodes, selected from among the two or more electrodes to which the pacing pulses are administered or from other electrodes in a vicinity of one or more of the pacing sites, following administration of the pacing pulse at the respective sites. Application of the ETC signal at a given site occurs during a predetermined time period following the pacing pulse at or near that site, during which period cardiac cells stimulated by the ETC signal generally do not generate propagating action potentials responsive to the ETC.

Preferably, the ETC signal comprises a pulse train, which is delivered to the left ventricle so as to enhance the peak pulsatile pressure generated by the ventricle and/or to achieve greater hemodynamic efficiency, most preferably resulting in larger cardiac output. The inventors have found that when ETC is combined with multi-site pacing, and particularly bi-ventricular pacing, cardiac output generally increases relative to the greatest cardiac output achievable with multi-site pacing alone.

Further preferably, the pacing signal is administered through one or more of the electrodes that are afterwards used to apply the ETC signal. Applying the ETC pulse train using the electrodes that were used a short time previously for pacing the left ventricle ensures that ETC-induced potential changes in the heart tissue will follow substantially the same electrical pathways as were taken by the earlier pacing-induced potentials. Therefore, new action potentials will generally not propagate in the affected tissue due to the ETC.

The present patent application teaches that multi-site pacing can be used to achieve optimal electrical synchronization of the ETC signal, for purposes of enhancing both hemodynamic performance and safety. Methods of multi-site pacing known in the art are concerned only with mechanical synchronization of the contraction of the heart chambers, while ETC stimulation can further increase cardiac performance by increasing cell contractility. The combination of mechanical resynchronization with enhanced contractility can be used to improve hemodynamics of cardiac patients beyond what can be achieved by multi-site pacing alone. The principles of the present invention may be applied in both implanted devices for cardiac pacing and stimulation and in external, bedside devices, primarily for treatment of hospitalized patients.

There is therefore provided, in accordance with a preferred embodiment of the present invention, a method for stimulating cardiac tissue, including:

applying pacing pulses to the heart at multiple sites in at least two different chambers of the heart; and applying an Excitable Tissue Control (ETC) signal in a vicinity of one or more of the pacing sites following application of the pacing pulse at the site.

Preferably, applying the pacing pulses includes pacing the left ventricle, and applying the ETC signal includes applying the signal in the left ventricle.

Further preferably, applying pacing pulses includes applying pacing pulses through at least one electrode coupled to the heart, and applying the ETC signal includes conveying the ETC signal through the at least one electrode. Preferably, applying the pacing pulses includes applying a pacing pulse to the left ventricle, and applying the ETC signal includes applying the signal in the left ventricle during a time period which begins between about 0 and 100 ms after onset of the pacing pulse applied to the left ventricle. More preferably, the time period begins between about 10 and 50 ms after application of the pulse to the left ventricle. Most preferably, the time period is selected so as to substantially eliminate the possibility that the ETC signal will cause an action potential to propagate in the tissue.

Preferably, applying the ETC signal includes conveying electrical energy to cells of the heart, such that action potentials are generally not generated in the cells responsive to the application of the ETC signal.

Further preferably, the ETC signal is applied in order to improve hemodynamic performance of the heart. Preferably, the ETC signal is applied in order to increase contractility of the heart or, alternatively or additionally, in order to increase systolic pressure generated by the heart.

In a preferred embodiment, applying the ETC signal includes sensing a physiological variable and applying the signal responsive thereto. Preferably, sensing the variable includes detecting an electrical depolarization wave in the tissue. Alternatively, sensing the variable includes sensing a hemodynamic parameter. Preferably, applying the pacing pulses include controlling application of the pacing pulses responsive to the variable, wherein controlling the application of the pacing pulses includes making a transition from a first stimulation mode to a second stimulation mode responsive to the variable.

There is also provided, in accordance with a preferred embodiment of the present invention, apparatus for stimulating cardiac tissue, including:

a plurality of electrodes, which are placed at multiple sites in at least two different chambers of the heart; and an electrical control unit, which applies pacing pulses to two or more of the electrodes at respective pacing sites in the at least two different chambers, and which applies an Excitable Tissue Control (ETC) signal to at least one of the electrodes in a vicinity of one or more of the pacing sites following application of the pacing pulse at the site.

Preferably, the at least one of the electrodes to which the ETC signal is applied includes one of the electrodes to which the pacing pulses are applied.

Further preferably, at least one of the pacing sites is in the left ventricle, and the ETC signal is applied to an electrode in the left ventricle.

Preferably, the control unit applies the ETC signal between during a time period which begins between about 0 and 100 ms after the onset of a pacing pulse applied by the control unit, wherein the time period is set so as to substantially eliminate the possibility that a propagating action potential will be generated responsive to application of the ETC signal. Preferably, the time period begins between about 10 and 50 ms after the onset of the pacing pulse.

Preferably, the ETC signal is applied in order to increase contractility of the heart or, alternatively or additionally, in order to increase systolic pressure generated by the heart.

In a preferred embodiment, the apparatus includes a sensor, which senses a physiological variable, wherein the control unit receives an input from the sensor and applies the ETC signal responsive thereto. Preferably, the sensor detects an electrical depolarization wave in the tissue. Alternatively or additionally, the sensor senses a hemodynamic parameter or senses motion. Preferably, the control unit controls application of the pacing pulses responsive to the variable. Further preferably, the control unit makes a transition from a first stimulation mode to a second stimulation mode responsive to the variable.

The present invention will be more fully understood from the following detailed description of the preferred embodiments thereof, taken together with the drawings, in which:

DETAILED DESCRIPTION OF PREFERRED EMBODIMENTS

Figure 1:
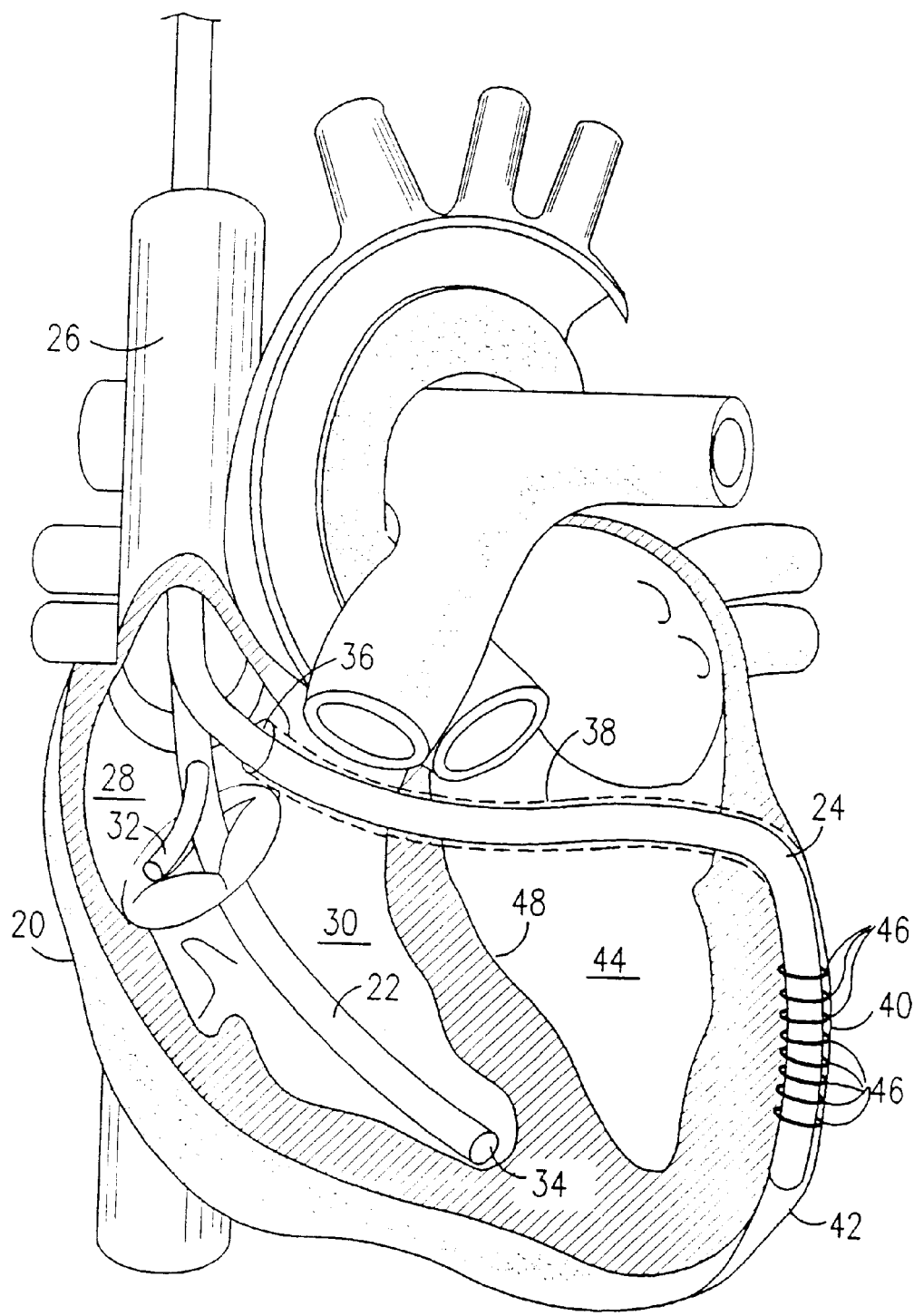
FIG. 1 is a schematic, sectional illustration of a heart, showing placement of pacing and ETC electrodes, in accordance with a preferred embodiment of the present invention.

FIG. 1 is a schematic, sectional view of a heart 20, illustrating insertion and placement of intracardiac catheters 22 and 24 for pacing and Excitable Tissue Control (ETC), in accordance with a preferred embodiment of the present invention. The catheters are preferably inserted into the heart through superior vena cava 26. Catheter 22 preferably places pacing electrodes 32 and 34, respectively, in the right atrium 28 and at the apex of the right ventricle 30 of the heart. Typically, electrodes 32 and 34 comprise unipolar electrodes, although bipolar electrodes may also be used, as is known in the pacing art. One or more electrodes 46, which preferably comprise a bipolar electrode pair or an array of electrodes, are placed in the left ventricle 44. Preferably, catheter 24 passes electrodes 46 from right atrium 28, through the coronary sinus 36 and the great coronary vein 38 to a mid-lateral site on the free wall 40 of left ventricle 44.

Other sites associated with left ventricle 44, such as elsewhere on free wall 40, on septum 48, or on the epicardium, may similarly be used for applying ETC stimulation. The ETC electrodes may operate in unipolar mode, as well as bipolar. Furthermore, other types of electrodes may be used, such as large-area electrodes, which allow a greater amount of energy to be applied in each stimulation pulse. Appropriate electrode types are described, for example, in PCT Patent Application PCT/IL97/00235, which is incorporated herein by reference. This application also describes the use of electrode arrays, including an addressable net of electrodes that is placed in left ventricle 44 and enables the loci and/or area over which the ETC stimulation is applied to be dynamically controlled.

Figure 2:
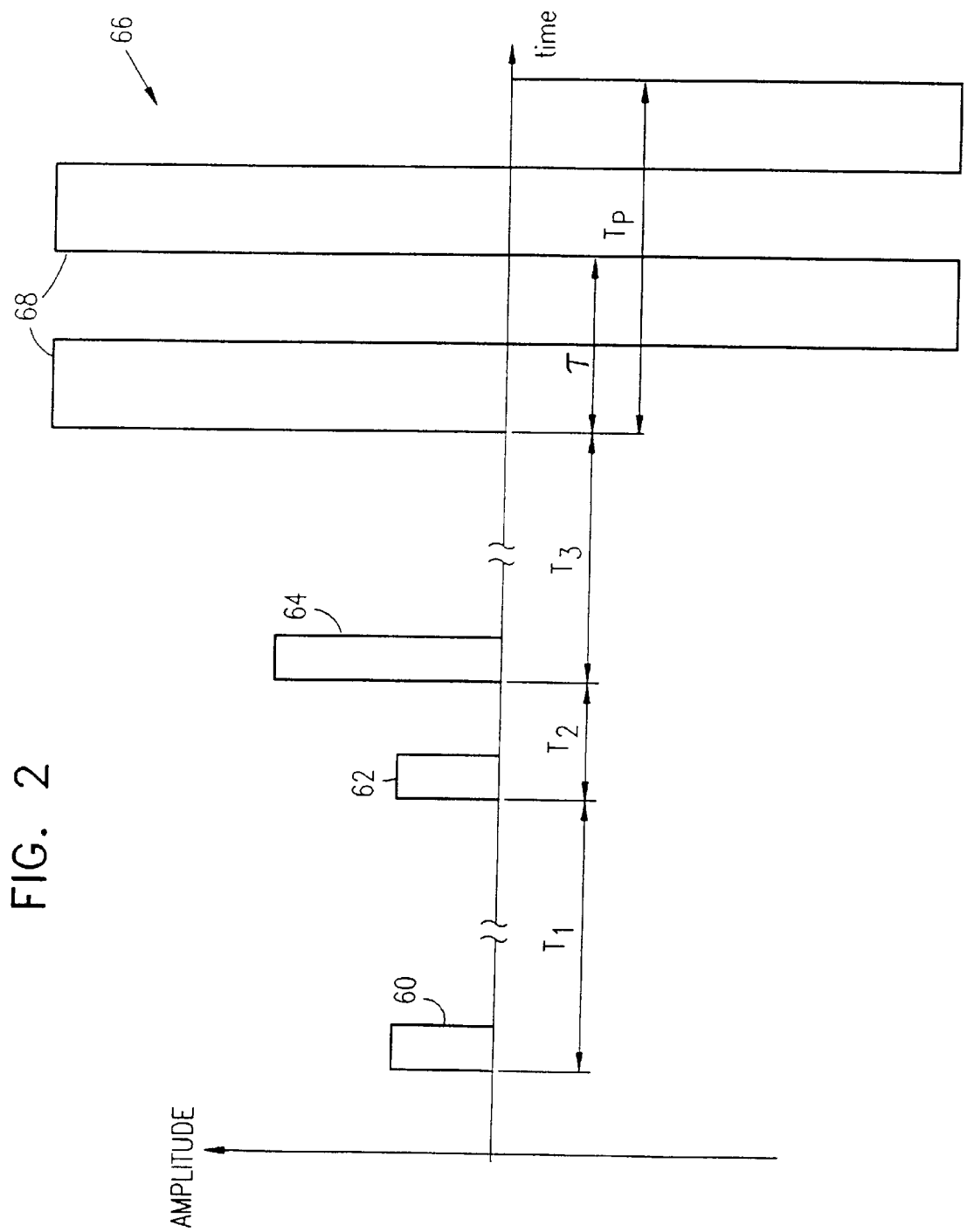
FIG. 2 schematically illustrates electrical signals applied to the electrodes of FIG. 1, in accordance with a preferred embodiment of the present invention.

FIG. 2 (not to scale) schematically illustrates electrical signals 66 applied to the electrodes of FIG. 1, in accordance with a preferred embodiment of the present invention. Electrical signals 66 comprise excitatory (pacing) pulses 60, 62, and 64, and non-excitatory (ETC) signals 68. Pacing pulses 60, 62, and 64 are preferably applied respectively to right atrium 28 by electrode 32, to right ventricle 30 by electrode 34, and to left ventricle 44 by electrodes 46. Biphasic ETC signals 68 are subsequently applied to the left ventricle by electrodes 46. ETC signals 68 are timed so as to be applied following pacing pulse 64, during a time period during which cells which were stimulated to contract by pacing pulse 64 will not generate propagating action potentials responsive to the application of ETC. Alternatively, biphasic pulses may be used instead of some or all of uniphasic pulses 60, 62, and 64. Further alternatively, ETC signals 68 may be uniphasic.

The duration of pulses 60, 62, and 64 typically is between about 0.5 and 2 ms, as is known in the pacing art. The time period T1 from the onset of pulse 60 until the onset of pulse 62 is preferably between approximately 60 and 200 ms, and is determined responsive to the desired delay between activation of right atrium 28 and right ventricle 30. Further preferably, the time period T2 from the onset of pulse 62 until the onset of pulse 64 is generally between about 0 and 80 ms, and is most preferably between approximately 5 and 20 ms. The time period T3 from the onset of pulse 64 until the onset of ETC signals 68 is generally between about 10 and 50 ms, most preferably between about 30 and 50 ms, and is determined such that the initiation and termination of ETC signals 68 occurs during the time period when cells stimulated by pulse 64 will generally not generate action potentials responsive to ETC signals 68. The amplitudes of pulses 60, 62, and 64 typically are respectively between about 0.5 and 4 V (2 and 3 V); 0.5 and 5 V (2 and 3 V); and 0.5 and 6 V (2 and 5 V), wherein the ranges given in parentheses are the preferred amplitudes for each pulse. Signal amplitudes may also be expressed in terms of electrical current, as is known in the art.

The period $\tau$ of biphasic ETC signals 68 is preferably between 5 and 20 ms, and the total duration $T_p$ of ETC application is typically between about 20 and 100 ms. The total, biphasic, amplitude of ETC signals 68 is preferably between about 2 and 20 V, most preferably between approximately 8 and 10 V.

Although FIG. 2 shows ETC signals 68 as a series of biphasic square wave pulses, it will be understood that other waveforms can also be used, such as a sinusoid, a sawtooth, a low-frequency square-wave pulse, or a combination of high- and low-frequency waveforms, as described, for example, in the above-mentioned PCT patent applications PCT/IL97/00235 and PCT/IL97/00236. The ETC waveforms may be either biphasic, as shown in FIG. 2, or uniphasic. The duty cycle of the waveform, defined in this context as the ratio of the positive portion of each signal relative to $\tau$ (wherein signals 68 is FIG. 2 have a duty cycle of 50%), may also be varied. Preferably, the shape, magnitude, and timing of ETC signals 68, as well as the timing of pacing pulses 60, 62 and 64, are optimized for each patient in order to attain a desired cardiac output. In this regard, the inventors have found that increasing the duty cycle of the ETC signals can increase the rate of onset of cardiac output enhancement following initiation of ETC stimulation.

The optimizing process is preferably performed in the presence of a physician, although for some applications it occurs automatically, at predetermined intervals, during the regular use of the pacing/ETC apparatus as provided by the present invention. A suitable process for optimization of the parameters of an ETC device is described in Israel Patent Application 127,295, which is assigned to the assignee of the present patent application and incorporated herein by reference.

Figure 3:
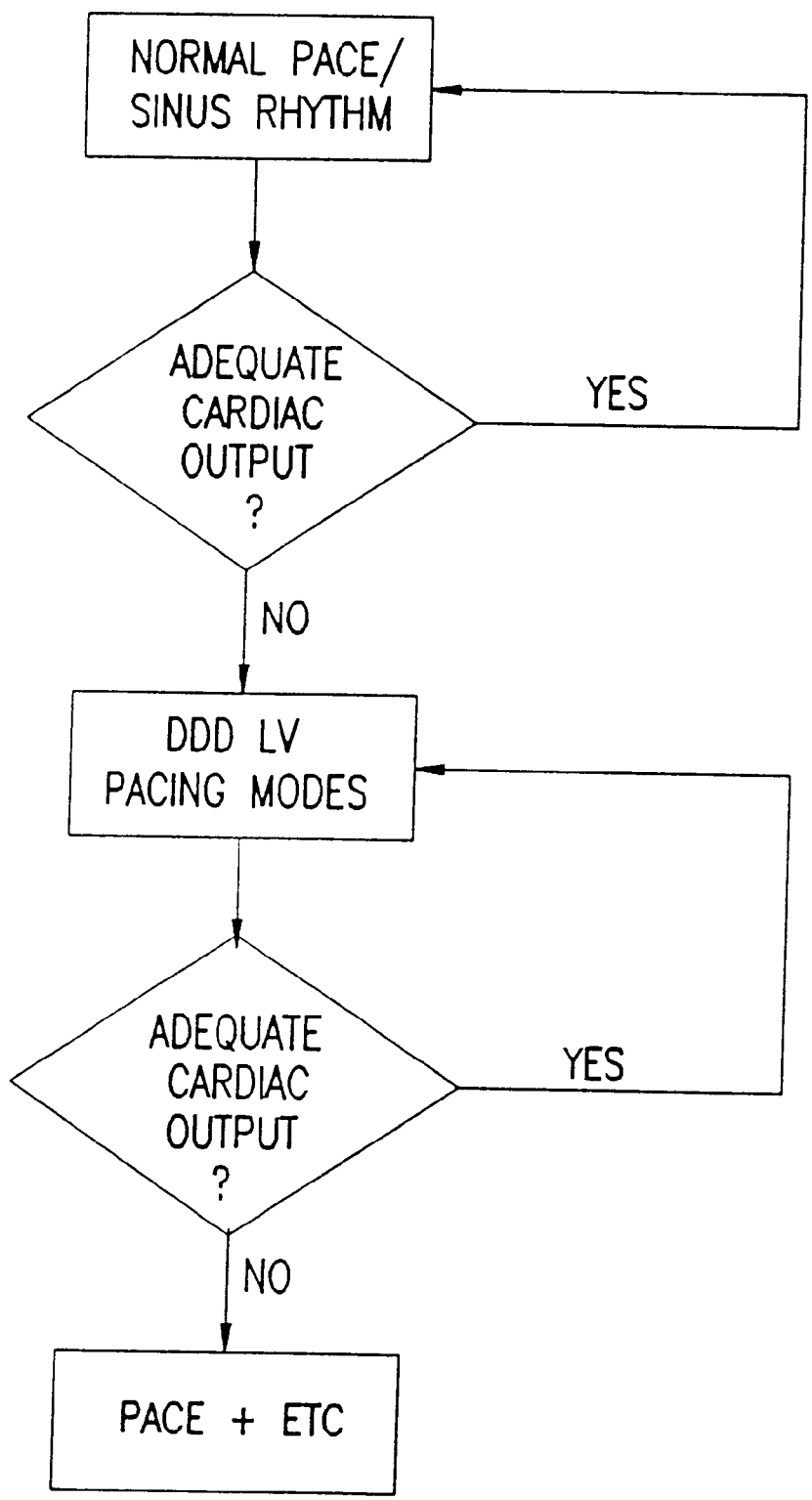
FIG. 3 is a flow chart that schematically illustrates a method for stimulating the heart, in accordance with a preferred embodiment of the present invention.
Figure 6:
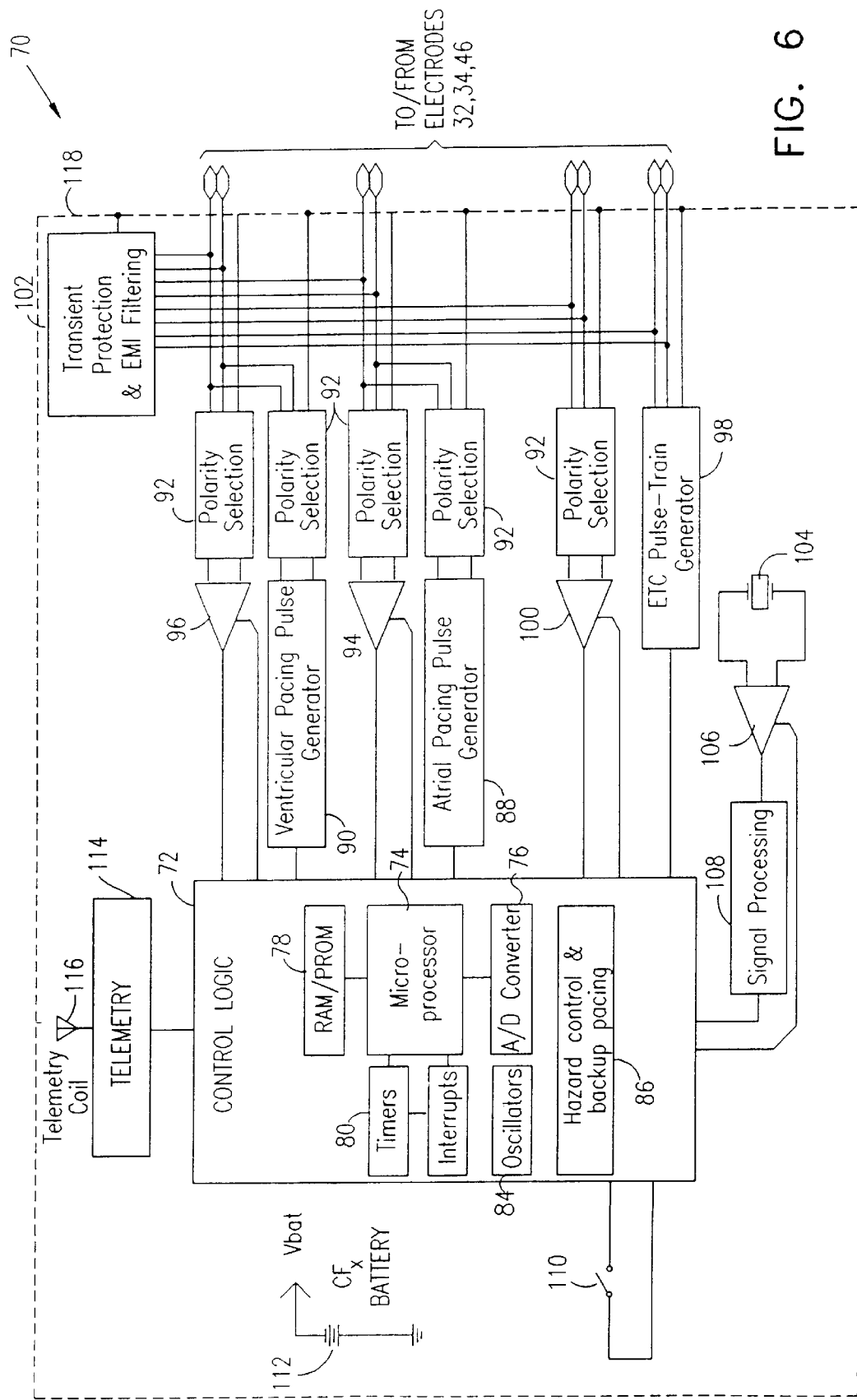
FIG. 6 is a schematic block diagram of a cardiac pacing and ETC device, in accordance with a preferred embodiment of the present invention.

FIG. 3 is a flow chart that schematically illustrates a method for graduated application of pacing and ETC signals, in accordance with a preferred embodiment of the present invention. Although FIG. 2 illustrates application of all of multiple pacing pulses 60, 62 and 64 and ETC stimulation 68, it is not always necessary to apply all of the pacing pulses or the ETC stimulation. Moreover, it is sometimes desirable to limit the electrical power that must be applied to the heart. Such power limitation is useful both in extending the battery lifetime of an implantable ETC device (as shown in FIG. 6 and described with reference thereto). It also allows the heart muscle to function in as natural a manner as physiological needs will allow and to rest when enhanced cardiac output is not required.

Thus, as illustrated in FIG. 3, in a default stimulation mode, the heart beats in sinus rhythm, or alternatively, only DDI pacing is applied to the heart, as is known in the art, without application of ETC stimulation. If it is determined that cardiac performance is inadequate, DDD pacing begins, which may further be supplemented by DDDR and/or biventricular pacing (pulse 64). Any other pacing mode known in the art may be incorporated in similar fashion, if appropriate. If pacing on its own still does not give adequate cardiac performance, the ETC stimulation is applied for a period of time.

The progression from mode to mode is preferably based on monitoring of hemodynamic parameters, such as cardiac output, flow and/or pressure. Additionally or alternatively, the progression from mode to mode is based on other criteria, such as parameters derived from analysis of electrical signals received from electrodes 32, 34 or 46. Such analysis may be used to detect variations in the heart rate, including detection of arrhythmias, as well as statistical heart rate variability. Analysis of heart rate and associated sensor readings may be used to determine when and how the ETC stimulation is to be applied, as described in the above-mentioned Israel Patent Application 127,295.

Furthermore, the general method of FIG. 3 may be applied in conjunction with graduated "fencing" (restriction of electrical/mechanical activity) of particular areas of cardiac tissue that are involved in arrhythmic conduction paths or undesirable muscular activity. Such fencing is described in the above-mentioned PCT Patent Application PCT/IL97/00012, as well as in PCT Patent Application PCT/IL97/00233, which is also incorporated herein by reference.

Figure 4:
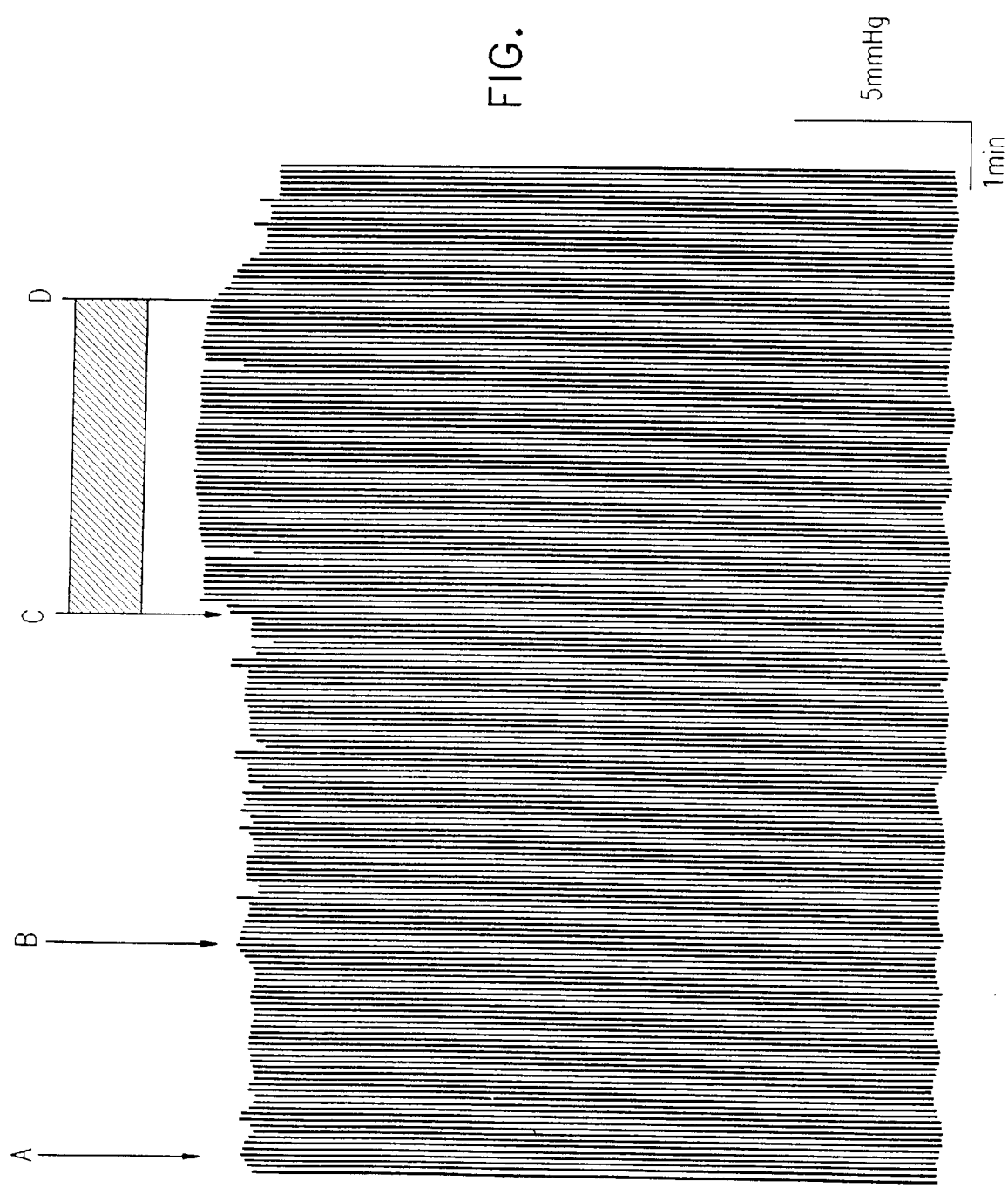
FIGS. 4 and 5 show experimental results obtained by application of the signals of FIG. 2.
Figure 5:
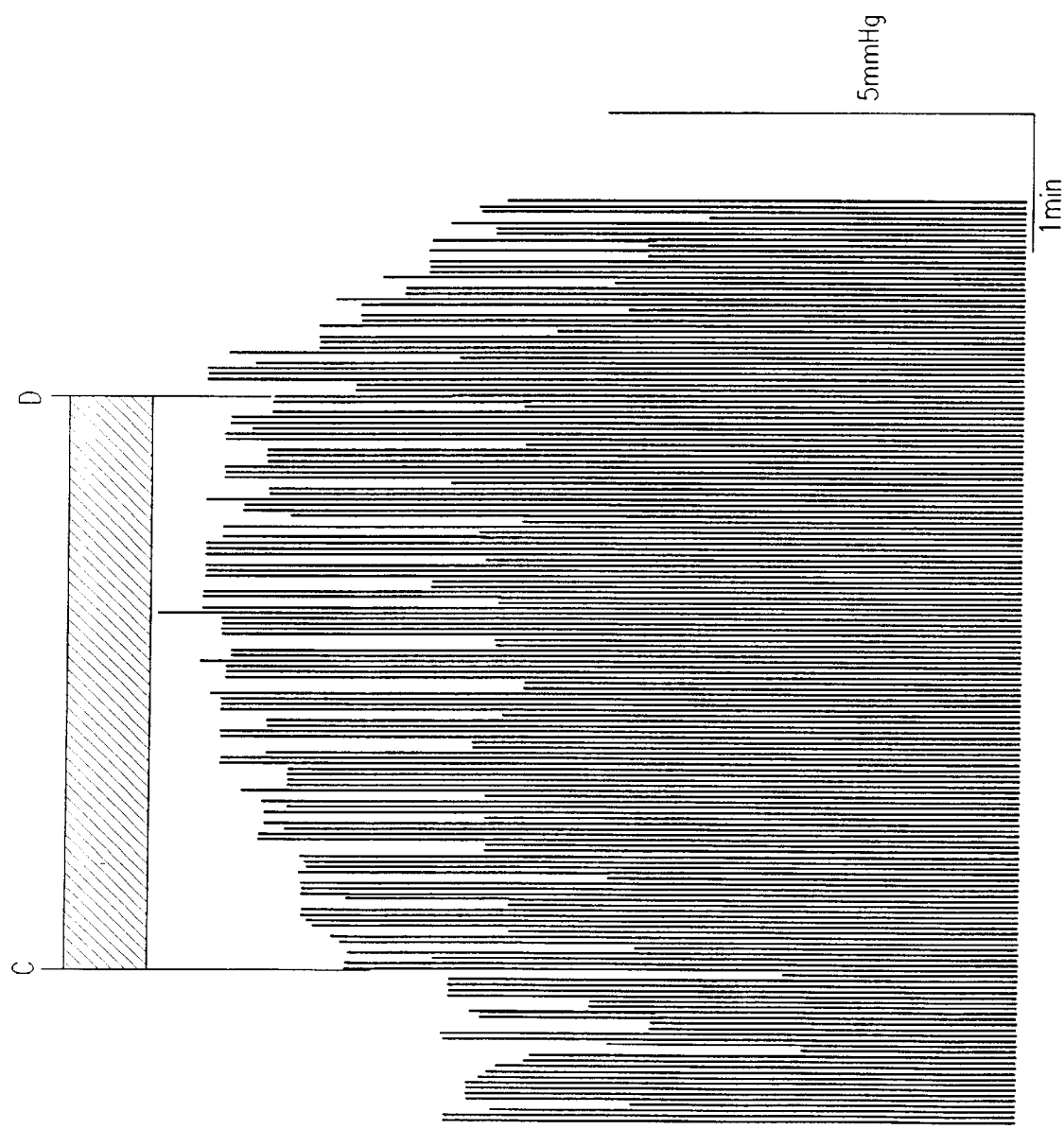

FIGS. 4 and 5 are graphs illustrating results of an experimental assessment of multi-site pacing with ETC, performed on a dog. Electrodes were placed as shown in FIG. 1, and electrical signals 66 were subsequently applied therethrough. It will be understood by one skilled in the art that although experimental data are shown with respect to a dog's heart, the principles of the present invention are expected to produce substantially parallel results in humans, with appropriate modification to the method and apparatus.

In the experiment, ordinary pacing electrodes, as are known in the art, were placed in right atrium 28 and right ventricle 30 of the dog's heart. Catheter 24 comprised an octopolar electrophysiology catheter having eight electrodes coupled thereto (manufactured by Cardima, Inc., Fremont, Calif.). Catheter 24 was inserted through coronary sinus 36 into the left anterior descending vein, adjacent to the free wall of left ventricle 44. A pair of the eight electrodes on the catheter was used for applying left ventricular pacing pulses 64 and ETC signals 68.

Right atrium 28 was first paced with a 2.5 volt, 2 ms pulse (pulse 60), followed 70 ms later by a similarly-shaped pulse to the right ventricle (pulse 62). Left ventricle 44 was paced 3.5 ms later with a 4.1 volt, 2 ms pulse (pulse 64). ETC signals 68 were applied 40 ms after the end of pulse 64. Thus, T1, T2, and T3 in the experiment were, respectively, 72 ms, 5.5 ms, and 42 ms. ETC signals 68 were applied using a τ of 10 ms and Tp of 20 ms. It will be understood, however, that these amplitude and timing values were specific to this particular experiment, and other values will be appropriate in different clinical situations.

FIGS. 4 and 5 show the experimental results obtained by application of the signals described hereinabove to the dog's heart. FIG. 5 shows, on expanded time and amplitude scales, a subset of the results shown in FIG. 4. The upper edge of each graph shows systolic pressure, and the lower edge in FIG. 4 shows diastolic pressure. Four time-points, A, B, C, and D, are shown in FIG. 4, representing the time of initiation of four respective modes of cardiac pacing. Points C and D also appear in FIG. 5.

Between points A and B, the dog's heart was paced in DDI mode, following generally the method of FIG. 3. Subsequently, between points B and C, biventricular DDD-mode pacing, including pacing of the left ventricle, was applied for several minutes. Throughout this baseline period between points A and C (i.e., prior to application of ETC stimulation, as provided by the present invention), the systolic pressure remained generally about 75 mm Hg.

At point C, ETC signals 68, as described hereinabove, were initiated, and DDD/biventricular pacing was continued. FIG. 4 shows that when the ETC stimulation commenced, the systolic pressure increased gradually, over the course of about one minute, to about 83 mm Hg. The increase is shown on expanded time and amplitude scales in FIG. 5. FIG. 4 shows no significant changes in the diastolic pressure responsive to application of the ETC stimulation. ETC signals 68 were continued for several minutes, and discontinued at point D. Subsequent to time-point D, the systolic pressure gradually dropped back to its previous level.

The experiment thus shows the effectiveness of ETC stimulation in enhancing cardiac performance relative to that obtained using multi-site, biventricular pacing alone. Enhanced performance is also achieved when the ETC stimulation is applied not after every pacing pulse, but rather intermittently relative to the pacing pulses. Furthermore, as noted above, because left ventricle 44 is paced shortly before the ETC stimulation, at or near the same site, the heart tissue stimulated by the pacing pulse generally is not susceptible to generation of action potentials responsive to the subsequent ETC stimulation. It will be understood that although the experiment described hereinabove was performed in the context of ETC and multi-site, biventricular pacing, the principles of the present invention can also be applied using a device capable of defibrillating the heart, in addition to biventricular pacing and ETC.

FIG. 6 is a schematic block diagram of a cardiac pacing and ETC device 70, in accordance with a preferred embodiment of the present invention. Device 70 preferably comprises a can 118, which encases circuitry of device 70. A control logic unit 72, inside can 118, is coupled to control the application of electrical energy from electrodes 32, 34, and 46 to heart tissue. A battery 112, typically inside can 118, provides power for the operation of device 70. A lithium-carbon-monofluoride (CFx) battery is suitable for most applications of the present invention.

As described hereinabove, application of ETC generally requires that the tissue stimulated by the ETC be in such a state that action potentials will not propagate in the tissue responsive to the ETC. Therefore, ETC signals are preferably delivered to the left ventricle following a suitable delay after the left ventricular pacing pulse. Most preferably, the ETC signals are applied at or near the site where a pacing pulse was applied, generally not later than about 30–50 ms thereafter. Additionally or alternatively, control logic unit 72 monitors electrical activity of the myocardium in the region of electrodes 46 using a local-activity sense (LS) amplifier 100, which senses passage of the depolarization wavefront generated by the left ventricular pacing pulse (or due to natural conduction in the heart tissue, when the left ventricle is not paced) and generates an electrical signal responsive thereto.

Although LS amplifier 100 is typically coupled to electrodes 46, in some preferred embodiments, the amplifier is coupled to another electrode or to an array of electrodes (such as a bipolar pair or other configurations including the ETC electrodes) in close proximity to the ETC electrodes, preferably within 1–20 mm thereof. For example, if octopolar catheter 24 (FIG. 1) is used, one pair of electrodes 46 may be used for applying the ETC stimulation, and another pair for sensing. Alternatively, the ETC stimulation may be applied in a unipolar mode, for example, between one or more of electrodes 46 and can 118, or between one or more of the electrodes and an external return pad in contact with the patient's body when a bedside version of device 70 is used.

A ventricular sensing amplifier 96 and an atrial sensing amplifier 94 are preferably coupled to control logic unit 72 and respectively to electrodes 34 and 32, in order to allow control logic unit 72 to perform standard sensing functions with respect to right ventricle 30 and right atrium 28, as are generally known in the art. Typically, separate polarity selection units 92 are coupled between amplifiers 96 and 94 and their respective electrodes, and are actuated by control logic unit 72 to select between unipolar and bipolar sensing and pacing modes, responsive to the corresponding mode in which the electrodes to which they are coupled are being paced.

Responsive to signals output by control logic unit 72, ventricular and atrial pacing pulse generators 90 and 88 coupled thereto generate and convey to electrodes 34 and 32 pacing pulses, whose magnitude, duration, and timing are specified by control logic unit 72. These pulse generators function in generally the same manner as similar pacing pulse generators known in the art. In addition to the two polarity selection units described hereinabove, an additional polarity selection unit 92 is preferably coupled between each of the pulse generators and its respective electrodes, in order to select a unipolar or bipolar pacing mode and to select the polarity of the pacing pulses.

Control logic unit 72 preferably comprises a microprocessor 74, which executes a pacemaking-ETC algorithm stored in a memory 78, preferably comprising RAM and PROM, coupled to the microprocessor. Additional electronic components coupled to the microprocessor preferably include timing circuitry, such as timers and interrupt generators 80 and oscillators 84, an A/D converter 76 for digitizing input signals from amplifiers 94, 96 and 100, a hazard control and backup pacing unit 86, and other circuitry known in the art of cardiac stimulation.

When it is determined by the pacemaking-ETC algorithm that left ventricle 44 should be paced, the pacing is preferably applied using ETC electrodes 46, although specialized pacing electrodes may also be used. The optimal timing and pulse parameters for the pacing of the left ventricle depend on factors such as the pacing sites, the event that originated the pacing cycle (paced or sensed event), the heart rate, and any known conduction problem existing in the heart itself.

Preferably, device 70 comprises a telemetry unit 114 coupled to a bi-directional telemetry coil 116 and to control logic unit 72. Further preferably, a reed switch 110, coupled to control logic unit 72, changes its state responsive to the presence of a magnet over the implant site, in order to cause control logic unit 72 to enter a telemetry mode. Unit 114 and coil 116 generally perform similar functions to those performed by pacemaker telemetry apparatus known in the art. In some applications of the present invention, for example, unit 114 allows a physician to use an interface "wand" coupled to a computer, in order to assess the state of battery 112, to change operating parameters of the device, to receive diagnostic data from the device, etc.

In order to enable control logic unit 72 to regulate pacing and ETC functions responsive to a subject's physical activity level, device 70 preferably comprises an accelerometer 104, an amplifier 106 coupled to amplify low-level signals generated by the accelerometer responsive to movement of the subject, and a signal processing unit 108 coupled to the amplifier and to control logic unit 72. Typically, accelerometer 104 comprises a piezoelectric crystal, which creates an electric field responsive to the deformation thereof.

Additionally or alternatively, as noted hereinabove, other detection modes are used by control logic unit 72 to regulate pacing and ETC functions. For example, unit 72 may receive signals based on detection of blood pressure in one or more locations in or near the heart at one or more times relative to systole and diastole. In a particular preferred detection mode, a pressure sensor (not shown) is implanted in one of the chambers of the heart, preferably in the left or right atrium, and is used to measure end-diastolic pressure. Controller 70 receives the pressure reading, and uses the pressure information to modulate pacing rate and ETC signal parameters. Alternatively, other types of sensors and measurements may be used, such as a flow rate, temperature, oxygen saturation, or substantially any other suitable sensor known in the art.

A unit 102 for protection against electrical transients and electromagnetic interference is typically coupled to output leads of device 70, which connect the device to electrodes 32, 34, and 46. Preferably, unit 102 is constructed generally in the same manner as medical electrical protection apparatus known in the art.

Figure 7:
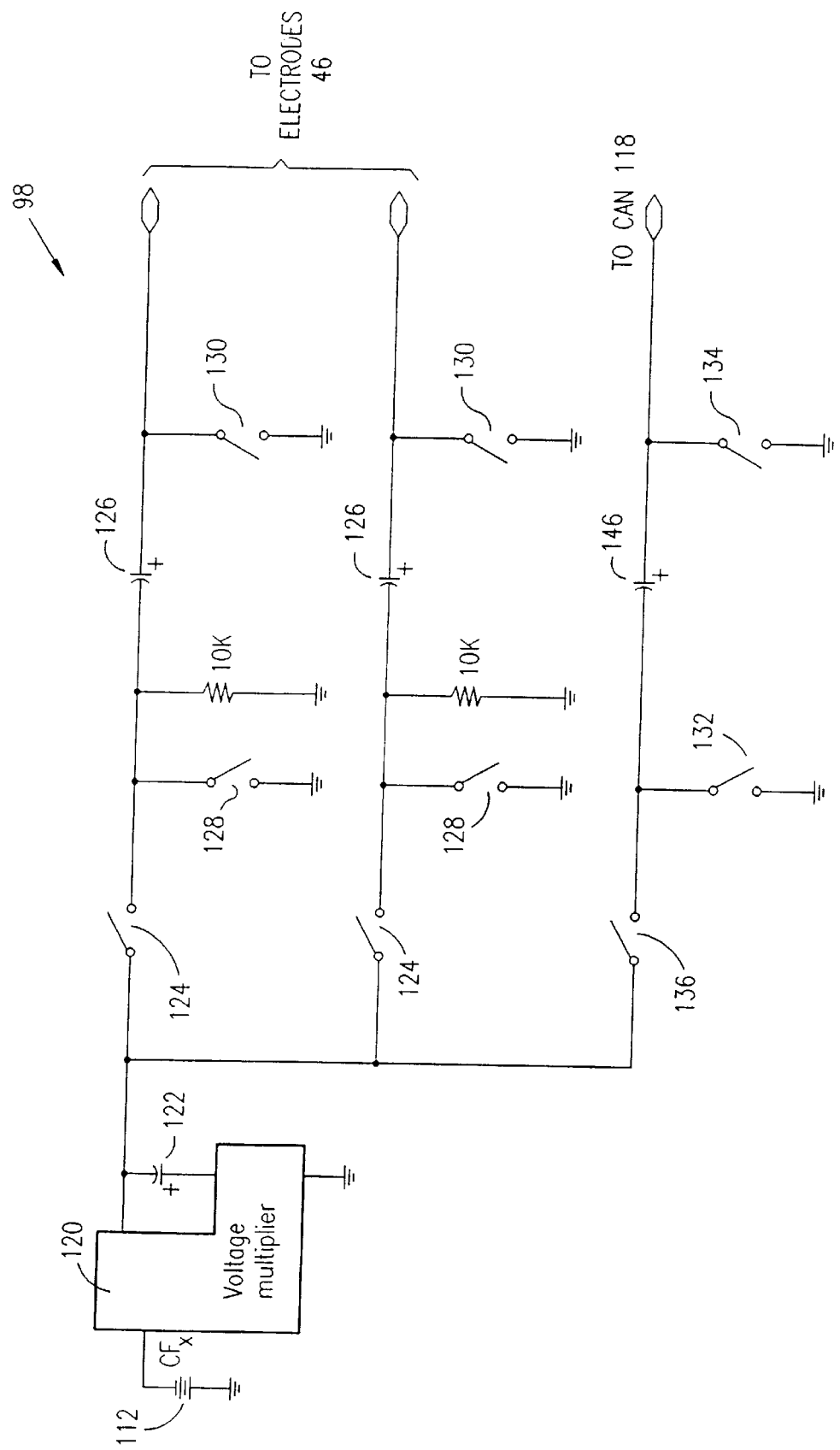
FIG. 7 is a schematic circuit diagram illustrating details of the device of FIG. 6, in accordance with a preferred embodiment of the present invention.

FIG. 7 is a schematic circuit diagram illustrating details of an ETC pulse-train generator 98 (also shown in FIG. 6), which is coupled to control logic unit 72, can 118, and electrodes 46, in accordance with a preferred embodiment of the present invention. In a typical mode of operation, a voltage multiplier 120 coupled to battery 112 charges a tank capacitor 122. Using circuitry described hereinbelow, control logic unit 72 subsequently initiates a discharge phase of capacitor 122, in which current is conveyed to electrodes 46 and/or can 118, in order to generate ETC signals 68. Repeated charging and discharging of tank capacitor 122 is used in this embodiment to generate a uniphasic or biphasic ETC pulse-train, as described hereinabove with respect to FIG. 2.

During the discharge phase, one or both of two switches 124 in pulse-train generator 98 are actuated by control logic unit 72 to close, in order to allow a pulse of current to go from tank capacitor 122 via DC blocking capacitors 126 to electrodes 46. Alternatively or additionally, a switch 136, controlled by control logic unit 72, is closed during the discharge phase, in order to allow current to be conveyed from tank capacitor 122 via a DC blocking capacitor 146 to can 118. Thus, the output pulse at electrodes 46 can be positive or negative with respect to can 118.

In a preferred mode of operation, the output of voltage multiplier 120 is generally positive with respect to ground, and control logic unit 72 actuates the closing of switches 124 in alternation, in order to enable biphasic output from electrodes 46.

Preferably, passive elements (e.g., 10 kΩhm resistors) are coupled to DC blocking capacitors 126 and 146 to enable the blocking capacitors to discharge current passively to ground. Active discharge elements 128 and 132, coupled respectively to DC blocking capacitors 126 and 146, preferably comprise switches controlled by control logic unit 72 to enable rapid discharging of the blocking capacitors to ground. Further preferably, active discharge elements 130 and 134, coupled respectively to electrodes 46 and can 118, comprise switches controlled by control logic unit 72 to create a low resistance path for return of ETC-induced currents following ETC stimulation.

Although operation of device 70 is described hereinabove with reference to certain preferred modes of operation, those skilled in the art will appreciate that the principles embodied in the device and in various elements and subassemblies thereof may advantageously be used in other stimulation modes and operational contexts. For example, elements of device 70 may used in combination with a defibrillating device. Such a combination is particularly advantageous for patients suffering from congestive heart failure (CHF), since in addition to the problems of inadequate cardiac output caused by CHF, such patients are also frequently at risk of developing ventricular fibrillation. Defibrillation pulses, when required, may be applied either between pairs of the electrodes applied to the heart or between one or more of the electrodes and the can.

All such variations, applications and sub-combinations of elements are considered to be within the scope of the present invention. It will thus be appreciated that the preferred embodiments described above are cited by way of example, and the full scope of the invention is limited only by the claims.

What is claimed is:

1. A method for stimulating cardiac tissue, comprising:
   providing a plurality of electrodes in at least two different chambers of the heart;
   applying bi-ventricular pacing pulses to the heart at multiple sites in at least two different chambers of the heart; and
   applying an Excitable Tissue Control (ETC) signal in a vicinity of one or more of the pacing sites located in the left ventricle following application of the pacing pulse at said site.

2. A method according to claim 1, wherein the ETC signal is applied during a time period which begins between about 0 and 100 ms after onset of the pacing pulse applied to the left ventricle.

3. A method according to claim 2, wherein the time period begins between about 10 and 50 ms after application of the pulse to the left ventricle.

4. A method according to claim 2, wherein the time period is selected such that the ETC signal does not cause an action potential to propagate in the tissue.

5. A method according to claim 1, wherein the ETC signal is applied in response to a sensed physiological variable.

6. A method according to claim 5, wherein the physiological variable sensed is an electrical depolarization wave in the tissue.

7. A method according to claim 5, wherein the physiological variable sensed is a hemodynamic parameter.

8. Apparatus for stimulating cardiac tissue, comprising:

a plurality of electrodes suitable to be placed at multiple sites in at least two different chambers of the heart; and an electrical control unit, suitable to apply pacing pulses to two or more of the electrodes and which, at the same time, is suitable to apply an Excitable Tissue Control (ETC) signal to at least one of the electrodes following application of the pacing pulses therethrough.

9. Apparatus according to claim 8, wherein the at least one of the electrodes to which the ETC signal is applied is one of the electrodes to which the pacing pulses are applied.

10. Apparatus according to claim 8, wherein the control unit applies the ETC signal between during a time period which begins between about 0 and 100 ms after the onset of a pacing pulse applied by the control unit.

11. Apparatus according to claim 10, wherein the time period is set such that it does not generate a propagating action potential responsive to application of the ETC signal.

12. Apparatus according to claim 10, wherein the time period begins between about 10 and 50 ms after the onset of the pacing pulse.

13. Apparatus according to claim 8, comprising a sensor suitable to sense a physiological variable, said sensor generating an input which is received by the control unit, said control unit applying the ETC signal responsive thereto.

14. Apparatus according to claim 13, wherein the sensor is an electrical depolarization wave sensor.

15. Apparatus according to claim 13, wherein the sensor is a sensor of a hemodynamic parameter.

16. Apparatus according to claim 13, wherein the sensor is a motion sensor.

* * * * *

UNITED STATES PATENT AND TRADEMARK OFFICE
CERTIFICATE OF CORRECTION

PATENT NO.         : 6,292,693 B1                           Page 1 of 1
APPLICATION NO. : 09/260769
DATED              : September 18, 2001
INVENTOR(S)        : Nissim Darvish and Itzhak Shemer It is certified that error appears in the above-identified patent and that said Letters Patent is hereby corrected as shown below:

On Title Page, Item (60) should read

--Related U.S. Application Data
(60) Provisional application No. 60/107,479, filed on November 6, 1998--

Column 1, line 7, "60/104,479" should read -- 60/107,479 --.

Signed and Sealed this

Tenth Day of April, 2007

JON W. DUDAS
*Director of the United States Patent and Trademark Office*